US012773404B2

(12) United States Patent
Zhang et al.

(10) Patent No.: US 12,773,404 B2
(45) Date of Patent: Oct. 27, 2026

(54) USE OF A CLASS OF 1,4-DIHYDRO-NAPHTHYRIDINE DERIVATIVES IN TREATMENT OF TUMORS

(71) Applicant: NEURODAWN PHARMACEUTICAL CO., LTD., Nanjing (CN)

(72) Inventors: Zhengping Zhang, Nanjing (CN); Fulong Li, Nanjing (CN); Lei Wang, Nanjing (CN); Rong Chen, Nanjing (CN); Weidong Yang, Nanjing (CN); Fang Fang, Nanjing (CN); Wenji An, Nanjing (CN); Yao Hua, Nanjing (CN); Lin Feng, Nanjing (CN)

(73) Assignee: NEURODAWN PHARMACEUTICAL CO., LTD., Nanjing (CN)

( * ) Notice: Subject to any disclaimer, the term of this patent is extended or adjusted under 35 U.S.C. 154(b) by 198 days.

(21) Appl. No.: 18/720,926

(22) PCT Filed: Nov. 21, 2022

(86) PCT No.: PCT/CN2022/133165

§ 371 (c)(1),
(2) Date: Jun. 17, 2024

(87) PCT Pub. No.: WO2023/116304

PCT Pub. Date: Jun. 29, 2023

(65) Prior Publication Data

US 2025/0057832 A1 Feb. 20, 2025

(30) Foreign Application Priority Data

Dec. 24, 2021 (CN) ......................... 202111599362.3

(51) Int. Cl.

| | |
|---|---|
| ***C07D 495/14*** | (2006.01) |
| ***A61K 31/4188*** | (2006.01) |
| ***A61K 31/4745*** | (2006.01) |
| ***A61P 35/00*** | (2006.01) |
| ***C07D 471/04*** | (2006.01) |

(52) U.S. Cl.

CPC ...... *A61K 31/4745* (2013.01); *A61K 31/4188* (2013.01); *A61P 35/00* (2018.01)

(58) Field of Classification Search

CPC . A61K 31/4745; A61K 31/4188; A61P 35/00; C07D 495/14; C07D 471/04; C07D 471/12

See application file for complete search history.

(56) References Cited

U.S. PATENT DOCUMENTS

| | | | |
|---|---|---|---|
| 8,461,179 B1 | 6/2013 | Flynn et al. | |
| 9,028,796 B2 | 5/2015 | Maltese et al. | |
| 9,284,330 B2 * | 3/2016 | Chen | A61P 3/14 |
| 10,675,257 B2 | 6/2020 | Guedat et al. | |
| 2014/0364443 A1 | 12/2014 | Chen et al. | |

FOREIGN PATENT DOCUMENTS

| | | | |
|---|---|---|---|
| CN | 103145704 | A | 6/2013 |
| CN | 104203945 | B | 1/2017 |
| CN | 106632317 | A | 5/2017 |
| CN | 110305128 | A | 10/2019 |
| EP | 2789613 | A1 | 10/2014 |
| WO | WO 2013/083070 | A1 | 6/2013 |

OTHER PUBLICATIONS

Bhanot, H. et al., "Induction of Nonapoptotic Cell Death by Activated Ras Requires Inverse Regulation of Rac1 and Arf6," *Molecular Cancer Research*, 8.10 (2010): 1358-1374.

Chi, S. et al., "Oncogenic Ras triggers cell suicide through the activation of a caspase-independent cell death program in human cancer cells," *Oncogene*, 18 (1999): 2281-2290.

D'Amore, C. et al., ""Janus" Efficacy of CX-5011: CK2 Inhibition and Methuosis Induction By Independent Mechanisms," *BBA-Molecular Cell Research*, (2020): 1-31.

Feng, L. et al., "Research progress on antitumor activity and structure-activity relationship of quinoline and nalidixic derivatives," *World Notes in Antibiotics*, 29.6 (2008): 268-282.

Li, Z. et al., "The JNK signaling pathway plays a key role in methuosis (non-apoptotic cell death) induced by MOMIPP in glioblastoma," *BMC Cancer*, 19.77 (2019): 1-20.

Maltese, W. A. et al., "Nonapoptotic Cell Death Associated with Vacuolization of Macropinosome and Endosome Compartments," *The American Journal of Pathology*, 184.6 (2014): 1631-1642.

Ostrom, Q. T. et al., "CBTRUS Statistical Report: Primary Brain and Other Central Nervous System Tumors Diagnosed in the United States in 2011-2015," *Neuro-Oncology*, 20.S4 (2018): 1-86.

PCT International Search Report and Written Opinion issued in International Patent Application No. PCT/CN2022/133165, mailed Jan. 17, 2023.

Robinson, M. W. et al., "Synthesis and Evaluation of Indole-Based Chalcones as Inducers of Methuosis, a Novel Type of Nonapoptotic Cell Death," *Journal of Medicinal Chemistry*, 55 (2012): 1940-1956.

Shubin, A. V. et al., "Cytoplasmic vacuolization in cell death and survival," *Oncotarget*, 7.34 (2016): 55863-55889.

Tan, A. C. et al., "Management of Glioblastoma: State of the Art and Future Directions," *Ca Cancer J Clin.*, 70 (2020): 299-312.

Extended European Search Report issued in European Patent Application No. 22909620.1, dated Oct. 30, 2025.

Marco-Contelles, J. et al., "Tacripyrines, the First Tacrine-Dihydropyridine Hybrids, as Multitarget-Directed Ligands for the Treatment of Alzheimer's Disease," *J. Med. Chem.*, 52 (2009): 2724-2732.

Office Action issued in Indian Patent Application No. 202417053152, dated Jul. 9, 2026.

Office Action issued in Philippine Patent Application No. Jan. 2024/551544, dated Jul. 24, 2026.

Xi, H-J. et al., "Role of acetylcholinesterase in lung cancer," *Thoracic Cancer*, 6 (2015): 390-398.

* cited by examiner

*Primary Examiner* — Sikarl A Witherspoon
(74) *Attorney, Agent, or Firm* — pH IP Law

(57) ABSTRACT

The present invention relates to the use of a class of 1,4-dihydro-naphthyridine derivatives in the treatment of tumors.

10 Claims, 7 Drawing Sheets

USE OF A CLASS OF 1,4-DIHYDRO-NAPHTHYRIDINE DERIVATIVES IN TREATMENT OF TUMORS

This application is a National Phase Application under 35 U.S.C. § 371 of International Application No. PCT/CN2022/133165, titled "USE OF A CLASS OF 1,4-DIHYDRO-NAPHTHYRIDINE DERIVATIVES IN TREATMENT OF TUMORS", filed on Nov. 21, 2022, which claims the priority of Chinese Patent Application No. 202111599362.3, filed with the China National Intellectual Property Administration on Dec. 24, 2021, and titled with "USE OF A CLASS OF 1,4-DIHYDRO-NAPHTHYRIDINE DERIVATIVES IN TREATMENT OF TUMORS", which are hereby incorporated by reference in their entireties.

FIELD

The present invention belongs to the field of pharmaceuticals, and relates to new use of a 1,4-dihydro-naphthyridine derivative, more particularly to use of a 1,4-dihydro-naphthyridine derivative in the manufacture of a medicament for treating a tumor. The tumor is a solid tumor, including nervous system tumors and non-nervous system tumors. The nervous system tumors include glioblastoma, neuroblastoma, etc., and the non-nervous system tumors include liver cancer, colon cancer, gastric cancer, etc.

BACKGROUND

Glioblastoma (GBM) is the most common malignant primary intracranial tumor, accounting for approximately 57% of all gliomas and 48% of all primary central nervous system (CNS) malignant tumors (Neuro-oncology, 2018. 20: p. iv1-iv86). The mortality rate of glioblastoma is extremely high. In the United States, the 1-year survival rate of glioblastoma patients from 2000 to 2014 was 41.4%, and the 5-year survival rate was only 5.8% (CA: a cancer journal for clinicians, 2020. 70 (4): p. 299-312). The cause of glioblastoma is still poorly understood; the only known possible causative factor is ionizing radiation. It also brings certain challenges to the prevention and treatment of glioblastoma.

According to the degree of malignancy, glioblastoma can be divided into grades I to IV. Among them, I and II are gliomas with low malignancy, and III and IV are gliomas with high malignancy. The treatment methods of glioblastoma mainly include surgical resection, radiotherapy, and systemic therapy (chemotherapy, targeted therapy). Among them, post-surgery temozolomide concurrent radiotherapy combined with adjuvant chemotherapy has become the standard regimen for newly diagnosed glioblastoma. In addition to temozolomide, the current main chemotherapy drugs include nitrosoureas, procarbazine, platinums, vinblastines, and camptothecins. However, the anti-tumor action mechanism of conventional chemotherapy drugs cannot meet today's clinical needs.

In eukaryotic cells, macropinocytosis is an important pathway for cells to internalize extracellular substances and dissolve molecules. The macropinocytosis process has a dual effect on tumor cells. In the case of nutrient deficiency, tumor cells can internalize extracellular nutrients through the macropinocytosis pathway, thereby promoting tumor cell growth. However, overactivation of the macropinocytosis process through drug treatment or abnormal expression of RAS gene can induce a new mode of death: methuosis.

Methuosis is a new proteasome-independent form of cell death, characterized by the cytoplasm being filled with a large number of vacuoles derived from macropinocytosomes. This mode of death was first discovered in glioblastoma cells (Oncogene, 1999. 18 (13): p. 2281-90). Further research found that this mode of death is triggered by changes in macropinocytosomes that are independent of clathrin, which eventually forms a large number of vacuoles, causing cell rupture and death (Journal of medicinal chemistry, 2012. 55 (5): p. 1940-56). Current research has found that a variety of molecules are involved in the formation of macropinosomes, including Ras, Rac1, Arf6, Rab7, etc. (The American journal of pathology, 2014. 184 (6): p. 1630-42). Rac1 can affect the formation of macropinocytosomes by regulating the assembly of actin. In addition, the activation of Rac1 can reduce activated Arf6 through the mediation of GIT-1, thereby hindering the circulation of macropinocytosomes (Molecular cancer research: MCR, 2010. 8 (10): p. 1358-74). In recent years, it has been found that some small molecule compounds induce methuosis of cells by activating mechanisms such as MKK4, INK and Rac1, including methamphetamine, indolyl chalcone, vaquinnol-1, MOMIPP, CX-5011, etc. (Oncotarget 2016, 7, 55863-55889; BMC cancer 2019, 19, 77; BBA-Molecular Cell Research 2020, 118807).

1, 4-dihydro-naphthyridine derivatives are compounds that can both inhibit acetylcholinesterase activity and block the influx of extracellular calcium ions into cells through calcium channels. By inhibiting the activity of cholinesterase, 1, 4-dihydro-naphthyridine derivatives can delay the hydrolysis rate of acetylcholine, increase the level of acetylcholine in the synaptic cleft, and achieve the effect of treating Alzheimer's disease and vascular dementia (Chinese Patent Nos. CN104203945B and CN106632317A). In addition, by inhibiting the influx of calcium ions, 1, 4-dihydro-naphthyridine derivatives can improve the tolerance of nerve cells to ischemia, expand cerebral blood vessels and improve cerebral blood supply, protect neurons, and effectively improve the cognitive function of patients with vascular dementia.

SUMMARY 1, 4-dihydro-naphthyridine derivatives are compounds that can inhibit the activity of acetylcholinesterase and block the influx of extracellular calcium ions into cells through calcium channels, which can be used to treat Alzheimer's disease and vascular dementia. Such compounds can induce methuosis of tumor cells through a new mechanism of action that does not rely on cholinesterase inhibition and calcium channel blocking, thereby exerting anti-tumor effects.

A purpose of the present invention is to provide a drug that can treat tumors through a new mechanism and effectively prolong the survival period of patients. The drug is a 1,4-dihydro-naphthyridine derivative or a pharmaceutically acceptable salt thereof.

In particular, the present invention provides use of a 1,4-dihydro-naphthyridine derivative represented by Formula I or a pharmaceutically acceptable salt thereof in the manufacture of a medicament for treating a tumor, Formula I

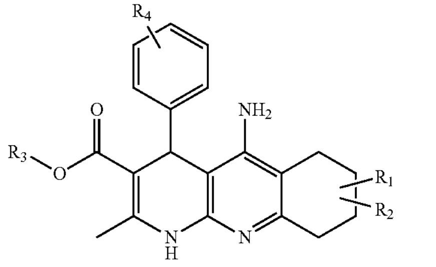

wherein, $R_1$ or $R_2$ is hydrogen, halogen or $C_1$-$C_6$ alkyl;

$R_3$ is selected from $C_1$-$C_6$ alkyl, wherein any —$CH_2$— in the alkyl may be replaced by one or more —O—;

$R_4$ is hydrogen or halogen.

In particular, the derivative is selected from the group consisting of:

S1

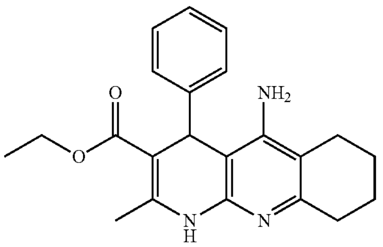

Compound 1 represented by S1;

S2

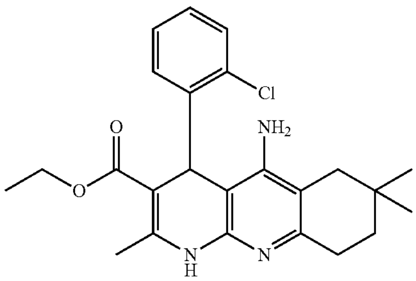

Compound 2 represented by S2;

S3

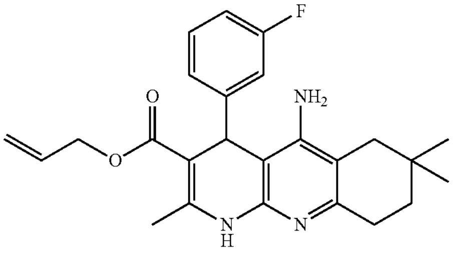

Compound 3 represented by S3;

S4

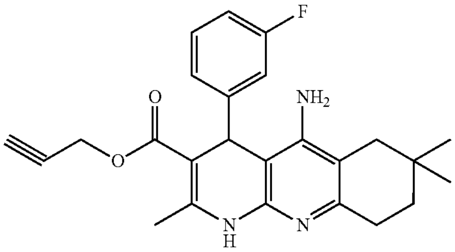

Compound 4 represented by S4;

S5

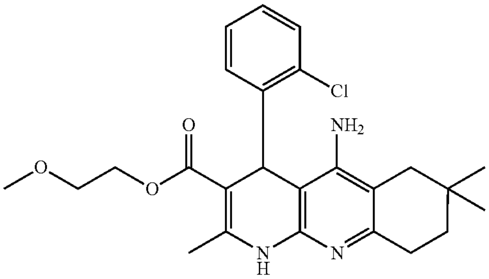

Compound 5 represented by S5; and

S6

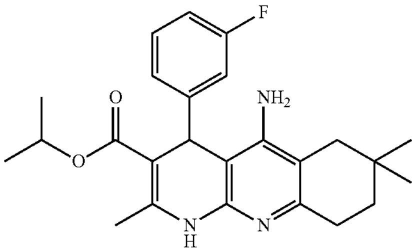

Compound 6 represented by S6.

The above compounds induce methuosis of tumor cells, cause vacuolated cell phenotype, inhibit the proliferation of tumor cells, and exert a function of inhibiting tumor growth, ultimately achieving the purpose of treating tumors.

Therefore, the present invention provides new use of a 1,4-dihydro-naphthyridine derivative or a pharmaceutically acceptable salt thereof or a pharmaceutical composition thereof in the manufacture of a medicament for treating a tumor.

The tumor is a solid tumor, including nervous system tumors and non-nervous system tumors. The nervous system tumors include glioblastoma, neuroblastoma, etc., and the non-nervous system tumors include liver cancer, colon cancer, gastric cancer, etc.

In particular, the present invention provides use of a 1,4-dihydro-naphthyridine derivative in the treatment of a solid tumor.

The present invention provides use of a 1,4-dihydro-naphthyridine derivative in the treatment of a nervous system tumor.

The present invention provides use of a 1,4-dihydro-naphthyridine derivative in the treatment of a brain tumor.

The present invention provides use of a 1,4-dihydro-naphthyridine derivative in the treatment of glioma.

The present invention provides use of a 1,4-dihydro-naphthyridine derivative in the treatment of glioblastoma.

The present invention provides use of a 1,4-dihydro-naphthyridine derivative in the treatment of liver cancer, colon cancer and gastric cancer.

The present invention provides use of a 1,4-dihydro-naphthyridine derivative combined with temozolomide in the treatment of glioma.

The present invention provides use of a 1,4-dihydro-naphthyridine derivative combined with radiotherapy in the treatment of glioma.

Advantages and Positive Effects of the Present Invention

As a new drug for treating tumors, the 1,4-dihydro-naphthyridine derivative provided by the present invention is a drug that specifically induces methuosis of tumor cells, which has little impact on normal cells, and is conducive to the development of safe and effective drugs to treat tumors.

DETAILED DESCRIPTION

Figure 1:
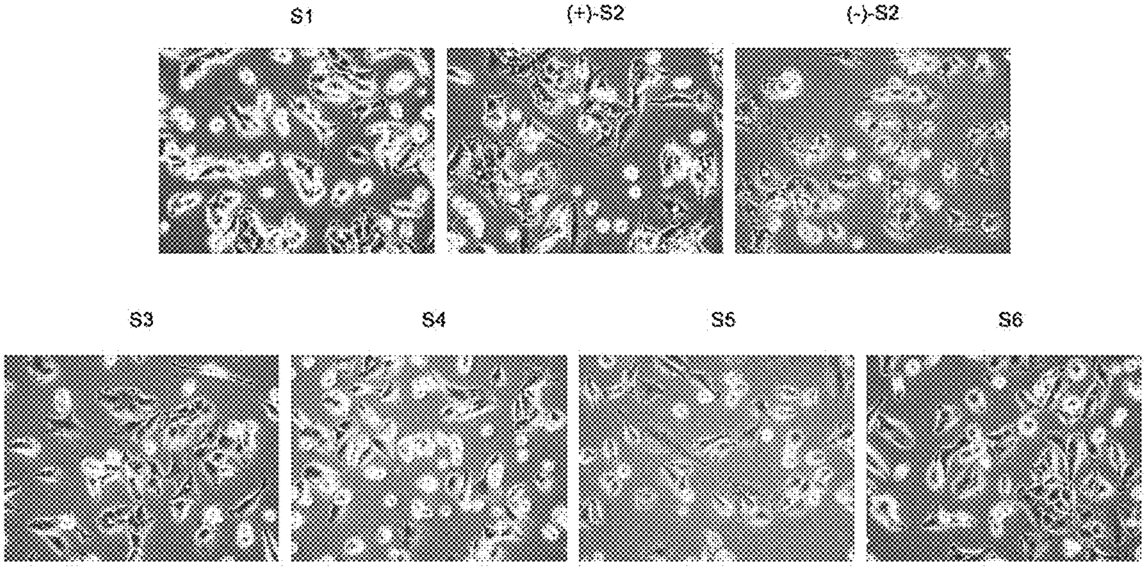
FIG. 1 shows that 1, 4-dihydro-naphthyridine derivatives induced vacuolation phenotype in T98 cells.
Figure 2:
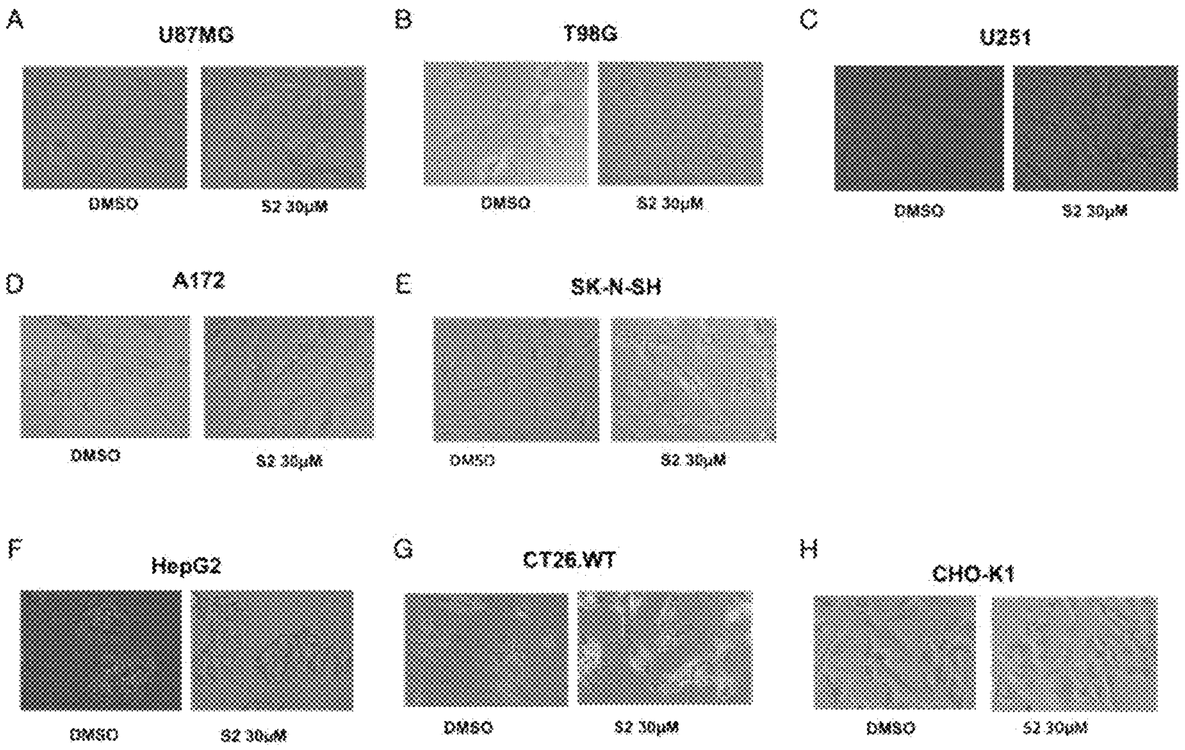
FIG. 2 shows that S2 induced vacuolation in various tumor cells.

The following examples illustrate the present invention and should not be considered as limiting the present invention.

Example 1 Study on the Vacuolation-Inducing and Proliferation-Inhibitory Effects of 1,4-dihydro-naphthyridine Derivatives on Glioblastoma Cells

1 Materials and Methods

1.1 Cells

Human nerve glioma cell line T98G cells were purchased from Nanjing Cobioer Biotechnology Co., Ltd.

1.2 Number and Structure of 1, 4-dihydro-naphthyridine Derivatives

| Number of compound | Structure |
|---|---|
| S1 | 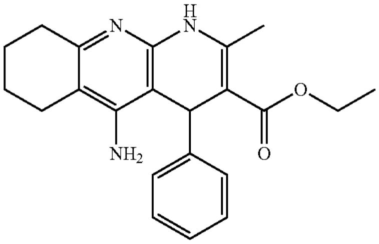 [SMILES: CCOC(=O)C1=C(C)Nc2nc3c(c(N)c2C1c1ccccc1)CCCC3] |
| (+)-S2 | 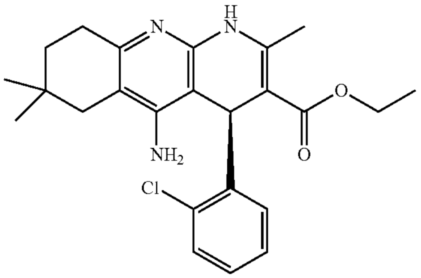 [SMILES: CCOC(=O)C1=C(C)Nc2nc3c(c(N)c2[C@@H]1c1ccccc1Cl)CC(C)(C)CC3] |
| (−)-S2 | 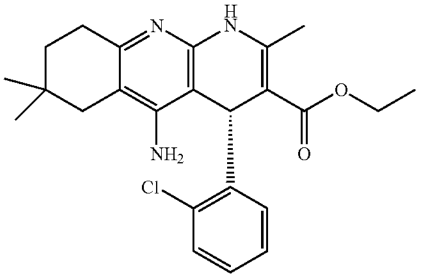 [SMILES: CCOC(=O)C1=C(C)Nc2nc3c(c(N)c2[C@H]1c1ccccc1Cl)CC(C)(C)CC3] |
| S3 | 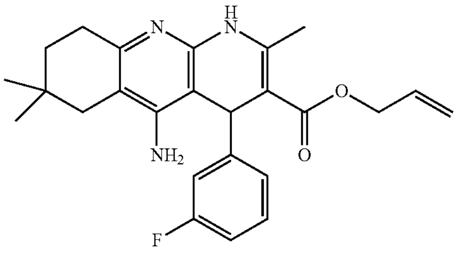 [SMILES: C=CCOC(=O)C1=C(C)Nc2nc3c(c(N)c2C1c1cccc(F)c1)CC(C)(C)CC3] |

-continued

| Number of compound | Structure |
|---|---|
| S4 | 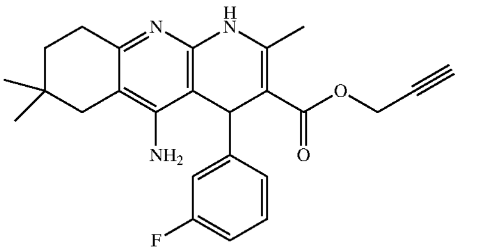 [SMILES: C#CCOC(=O)C1=C(C)Nc2nc3c(c(N)c2C1c1cccc(F)c1)CC(C)(C)CC3] |
| S5 | 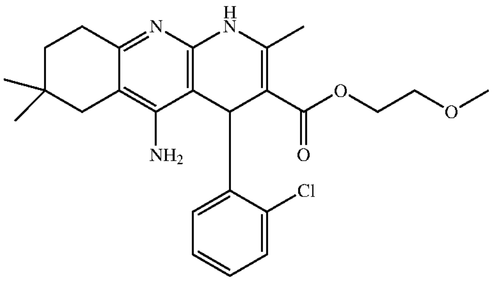 |
| S6 | 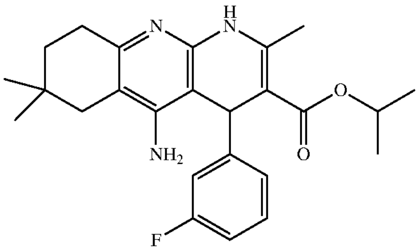 [SMILES: CC1=C(C(=O)OC(C)C)C(c2cccc(F)c2)c2c(nc3c(c2N)CC(C)(C)CC3)N1] |

1.3 Preparation of Compound Solution

A certain amount of the compound to be tested was weighed and dissolved with DMSO to prepare a uniform solution with a final concentration of 100 mM.

1.4 Reagents and Consumables

| Name | Cat no./Lot no. | Manufacturer |
|---|---|---|
| D-PBS | H106FA0001 | Sangon Biotech |
| Minimum Essential Medium | 2192505 | gibco |
| MEM NEAA(100×) | 2216384 | gibco |
| Sodium Pyruvate(100 mM) | 2192495 | gibco |
| Fetal Bovine Serum | 2261480CP | gibco |
| 0.05% Trypsin-EDTA | 2192791 | gibco |
| DMSO | 21020207 | TEDIA |
| Pen Strep | 2257223 | gibco |
| 12-well plate | 191204-075 | BioFIL |
| 96-well plate | 24820030 | Corning |

1.5 Cell Culture and Observation of Cell Phenotype

T98G cells were stably passaged twice. When the cell density reached more than 85%, the cells were digested with 0.05% trypsin-EDTA for 3 minutes, resuspended with the culture medium, and plated in a 12-well plate at a certain density, with each well system being 1 mL. The cells were cultured for 24 hours, and added with the compound solution prepared above to each well according to the grouping, so that the concentrations of the compounds in the culture system were respectively 5 μM, 10 μM, 20 μM, 40 μM, and 60 μM. An equal volume of DMSO was added as a control well.

After 6 hours of drug treatment, the plates were observed under a microscope with a 20× objective lens, and five fields of view were randomly selected for each well to take photos and record. If in the observed field of view, bright vacuoles with clear border appeared in the cell, and at least one of the following conditions was met: 1) a cell contained at least 1 vacuole with a diameter greater than 3 μm; 2) a cell contained 3 or more vacuoles with a diameter within the range of 0.5-3 μm, the cell was considered to be methuosis-positive cells.

$$\text{Vacuolization rate } R(\%) = \text{CELL}_{positive}/(\text{CELL}_{normal} + \text{CELL}_{positive}) \times 100\%$$

Among them, CELL positive: the number of methuosis-positive cells; CELL normal: the number of cells with normal morphology 1.6 Cell Proliferation Inhibition Assay T98G cells were stably passaged twice. When the cell density reached above 85%, the cells were digested with 0.05% trypsin-EDTA for 3 minutes, resuspended, plated in a 96-well plate at the corresponding density, and cultured for 24 hours. The cells were treated with drugs at final concentrations of the culture system of 0.41 μM, 1.23 μM, 3.7 μM, 11.1 μM, 33.3 μM, and 100 μM, respectively. After 72 hours of drug treatment, cell viability was determined using Cell-Counting-Lite™ 2.0 kit. The plate was added with reagents at 100 μL/well according to the CellCounting-Lite™ 2.0 kit instructions, and shaken for 10 minutes. The luminescence value (LUM) as read on a multi-function plate reader, and the relative viability of the cells was calculated.

Relative viability of tumor cells V (%)=(LUM−$LUM_{background}$)/($LUM_{normal\ control}$−$LUM_{background}$)×100%. $LUM_{background}$ was the background reading of the complete culture medium well added with the detection reagent. The half inhibitory concentration ($IC_{50}$) was calculated using GraphPad Prism 8.0.1 statistical software.

2 Experimental Results 2.1 1, 4-dihydro-naphthyridine Derivatives Induce Vacuolation in T98G Cells S1, S2 (including (+)-S2 and (−)-S2), S3, S4, S5 and S6 can induce vacuolation in T98 (FIG. 1 and Table 1), wherein S1 had the weakest vacuolation-inducing activity, and S2 had the strongest vacuolation-inducing activity.

TABLE 1

Quantitative analysis of vacuolation in T98G cells induced by 1,4-dihydro-naphthyridine derivatives

| Compound | Vacuolation rate (%) 5 μM | 10 μM | 20 μM | 40 μM |
|---|---|---|---|---|
| S1 | 0.0 | 0.3 ± 0.6 | 2.23 ± 0.5 | 10.0 ± 5.6 |
| (+)-S2 | 1.3 ± 1.6 | 10.0 ± 4.2 | 69.3 ± 6.9 | — |

TABLE 1-continued

| Quantitative analysis of vacuolation in T98G cells induced by 1,4-dihydro-naphthyridine derivatives | | | | |
|---|---|---|---|---|
| | Vacuolation rate (%) | | | |
| Compound | 5 μM | 10 μM | 20 μM | 40 μM |
| (−)-S2 | 1.2 ± 1.7 | 21.9 ± 9.0 | 96.47 ± 2.4 | — |
| S3 | 1.1 ± 1.5 | 5.34 ± 1.2 | 9.04 ± 3.8 | 57.4 ± 13.9 |
| S4 | 0.6 ± 1.4 | 5.0 ± 1.3 | 10.43 ± 1.0 | 76.9 ± 12.1 |
| S5 | 1.4 ± 1.4 | 10.7 ± 0.90 | 35.1 ± 1.3 | — |
| S6 | 0.00 | 10.5 ± 1.6 | 15.3 ± 1.3 | 52.3 ± 2.5 |

Data in the table are expressed as mean±SD; "-" indicates that the compound precipitated and the data was not calculated.

2.2 1, 4-dihydro-naphthyridine Derivatives Inhibit T98G Cell Proliferation 1, 4-dihydro-naphthyridine derivatives can inhibit the proliferation of neural tumor cells T98G. The tumor proliferation inhibitory activity $IC_{50}$ is shown in Table 2. The proliferation inhibitory activity of S1 is weak, which is basically consistent with the activity of inducing vacuolation.

TABLE 2

| Inhibitory activity of compounds on T98G cell proliferation | |
|---|---|
| Compound | IC50 |
| S1 | 47.8 μM |
| (+)-S2 | 5.3 μM |
| (−)-S2 | 9.8 μM |
| S3 | 7.0 μM |
| S4 | 12.7 μM |
| S5 | 4.5 μM |
| S6 | 20.5 μM |

Example 2 Study on the Inhibitory Activity of S2 on Tumor Cell Proliferation In Vitro

1 Materials and Methods

1.1 Cells

Human brain glioma cell line U87MG, human brain glioma cell line T98G and human brain glioma cell line U251 were purchased from Nanjing Cobioer Biotechnology Co., Ltd.; human brain glioma cell line A172, human neuroblastoma cell SK-N-SH, human liver cancer cell line HepG2, mouse colon cancer cell line CT26.WT and hamster ovary cell subline CHO-K1 were purchased from Wuhan Procell Biotechnology Co., Ltd.

1.2 Reagents and Consumables

| Name | Cat no./Lot no. | Manufacturer |
|---|---|---|
| D-PBS | H106FA0001 | Sangon Biotech |
| Minimum Essential Medium | 2192505 | gibco |
| MEM NEAA (100×) | 2216384 | gibco |
| Sodium Pyruvate (100 mM) | 2192495 | gibco |
| Fetal Bovine Serum | 2261480CP | gibco |

-continued

| Name | Cat no./Lot no. | Manufacturer |
|---|---|---|
| 0.05% Trypsin-EDTA | 2192791 | gibco |
| Pen Strep | 2257223 | gibco |
| CellCounting-Lite ™ 2.0 | DD1101-02 | Vazyme |
| 96-well plate | 24820030 | Corning |
| 6-well plate | 200421-074B | BioFIL |
| (−)-S2 | D12-20161101-7 | Jiangsu Simovay Pharmaceutical Co., Ltd. |
| DMSO | 21020207 | TEDIA |

1.3 Reparation of Drug Solution

S2 powder was precisely weighed, and dissolved with DMSO, to prepare a uniform solution with a concentration of 100 mM as the mother solution.

1.4 Cell Culture and Observation of Cell Phenotype

U87MG, T98G, U251, SK-N-SH, A-172 and HepG2 cells were adherently cultured in MEM+10% FBS+1% P/S medium and passaged at 1:3; CT26.WT cells were adherently cultured in RPMI-1640+10% FBS+1% P/S medium and passaged at 1:3; CHO-K1 was cultured adherently in Ham's F-12K+10% FBS+11% P/S medium and passaged at 1:3.

The cells used above were resuscitated and passaged twice stably. When the cell density reached above 85%, the cells were digested with 0.05% trypsin-EDTA for 3 minutes, resuspended with the culture medium, and plated into a 6-well plate at a certain density, with each well system being 2 mL. The cells were cultured for 24 hours, added with 2 μL of the above-prepared S2 solution (final DMSO concentration 0.1%) to each well according to the grouping, such that the S2 concentration in the cell culture system reached 30 μM.

After 6 hours of drug treatment, the plate was observed under a microscope with a 20× objective lens, and five fields of view were randomly selected for each well to take photos and record. If bright vacuoles with clear border appeared in the cell in the observed field of view, and at least one of the following conditions was met: 1) a cell contained at least one vacuole with a diameter greater than 3 m; 2) a cell contained 3 or more vacuoles with a diameter within the range of 0.5-3 m, the cell was considered as a methuosis-positive cell (Journal of Medicinal Chemistry 2018 61 (12), 5424-5434).

$$\text{Vacuolization rate } R(\%) = CELL_{positive} / (CELL_{normal} + CELL_{positive}) \times 100\%$$

$CELL_{positive}$: the number of methuosis-positive cells; $CELL_{normal}$: the number of cells with normal morphology

1.5 Cell Viability Assay

The above various cells were resuscitated and stably passaged twice. When the cell density reached above 85%, the cells were digested with 0.05% trypsin-EDTA for three minutes, resuspended, plated in a 96-well plate at the corresponding density, and cultured for 24 hours. The cells were treated with drugs at final concentrations of the culture system of 0.41 μM, 1.23 μM, 3.7 μM, 11.1 μM, 33.3 μM, and 100 μM. After 48 hours of drug treatment, cell viability was determined using CellCounting-Lite™ 2.0 kit. The plate was added with reagents at 100 L/well according to the CellCounting-Lite™ 2.0 kit instructions, and shaken for 10 minutes. The luminescence value (LUM) was read on a multi-function plate reader, and the relative viability of the cells was calculated.

Relative viability of tumor cells V (%)=$(LUM-LUM_{background})/(LUM_{normal\ control}-LUM_{background})\times100\%$. $LUM_{background}$ was the background reading of the complete culture medium well added with the detection reagent. The half inhibitory concentration ($IC_{50}$) was calculated using GraphPad Prism 8.0.1 statistical software.

2 Experimental Results

2.1 S2 Induces Vacuolization of Tumor Cells

S2 can induce vacuolation in neural tumor cells such as human glioma cell lines U87MG, T98G, U251 and A172, human neuroblastoma cell line SK-N-SH (FIGS. 2A-D), and can also induce vacuolation in non-nervous system tumor cells (FIGS. 2A-D), including human liver cancer cell HepG2 and mouse colon cancer cell CT26.WT. However, S2 could not induce vacuolation in the non-tumor cell line hamster ovary cell CHO-K1.

2.2 S2 Inhibits Tumor Cell Proliferation

S2 can inhibit the proliferation of neural tumor cells and non-neural tumor systems, with an $IC_{50}$ within the range of 4.7-14.3 μM, but had very weak inhibitory effect on the proliferation of non-tumor cell lines ($IC_{50}$>100 μM) (Table 3).

TABLE 3

Inhibitory effect of S2 on tumor cell proliferation

| Tumor cell | $IC_{50}$ (μM) |
|---|---|
| U87MG | 11.7 μM |
| T98G | 9.4 μM |
| U251 | 14.3 μM |
| SK-N-SH | 11.4 μM |
| A172 | 4.7 μM |
| HepG2 | 10.1 μM |
| CT26.WT | 7.1 μM |
| CHO-K1 | ~100 μM |

Example 3 Effects of AChE Inhibitors and VGCC Blockers on the Vacuolation Phenotype of T98 Cells

1 Materials and Methods

1.1 Cells

Human brain glioma cell line T98G was purchased from Nanjing Cobioer Biotechnology Co., Ltd.

1.2 Reagents and Consumables

| Name | Cat no./Lot no. | Manufacturer |
|---|---|---|
| D-PBS | H106FA0001 | Sangon Biotech |
| Minimum Essential Medium | 2192505 | gibco |
| MEM NEAA (100×) | 2216384 | gibco |
| Sodium Pyruvate (100 mM) | 2192495 | gibco |
| Fetal Bovine Serum | 2261480CP | gibco |
| 0.05% Trypsin-EDTA | 2192791 | gibco |
| Pen Strep | 2257223 | gibco |
| 12-well plate | 191204-075 | BioFIL |
| (−)-S2 | D12-20161101-7 | Jiangsu Simovay Pharmaceutical Co., Ltd. |
| Nifedipine | N7634 | Sigma |
| Diltiazem | 20210815 | Nanjing Chemlin Chemical Industry Co., Ltd. |
| Verapamil | C13156635 | Shanghai Macklin Biochemical Technology Co., Ltd. |
| Donepezil | DT6821 | Sigma |
| Flunarizine | AGN20-39525 | Shanghai Kaiwei Chemical Technology Co., Ltd. |
| DMSO | 21020207 | TEDIA |

1.3 Preparation of Drug Solution

The drugs to be tested include: nifedipine, verapamil, diltiazem, flunarizine and donepezil.

The above-mentioned drugs to be tested were precisely weighed, and dissolved with DMSO, to prepare a uniform solution with a concentration of 20 mM as the mother solution, respectively.

1.4 Cell Culture and Observation of Cell Phenotype

T98G cells were stably passaged twice. When the cell density reached more than 85%, the cells were digested with 0.05% trypsin-EDTA for 3 minutes, resuspended with the culture medium, and plated in a 12-well plate at a certain density, with each well system being 1 mL. The cells were cultured for 24 hours, and added with the compound solution prepared above to each well according to the grouping, such that the compound concentrations in the culture system were 0.1 μM, 1 μM, 5 μM, and 20 μM, respectively. An equal volume of DMSO was added as a control well.

After 6 hours of drug treatment, the plate was observed under a microscope with a 20× objective lens. If bright vacuoles with clear border appeared in the observed field of view, and at least one of the following conditions was met: 1) a cell contained at least one vacuole with a diameter greater than 3 μm; 2) a cell contained 3 or more vacuoles with a diameter within the range of 0.5-3 μm; the cell was considered as a methuosis-positive cell.

2 Experimental Results

Figure 3:
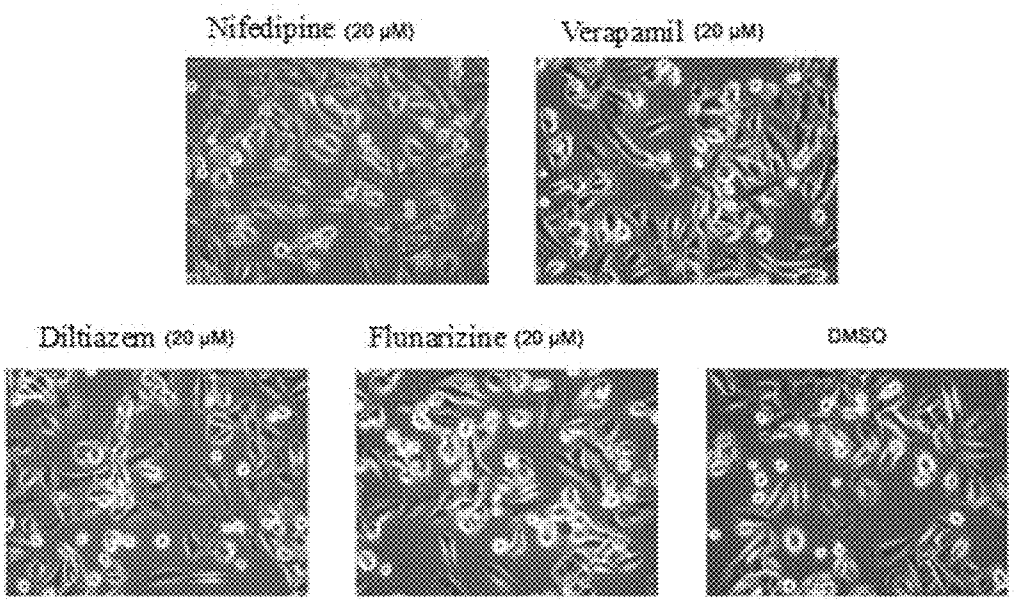
FIG. 3 shows that calcium channel inhibitors did not induce vacuolization of tumor cells.

2.1 Calcium Channel Inhibitors (VGCC) Failed to Induce Vacuolization of Tumor Cells None of calcium channel inhibitors nifedipine, verapamil, diltiazem, and flunarizine with a maximum drug concentration of 20 μM could induce a vacuolated cell phenotype of the human glioma cell line T98G (FIG. 3).

Figure 4:
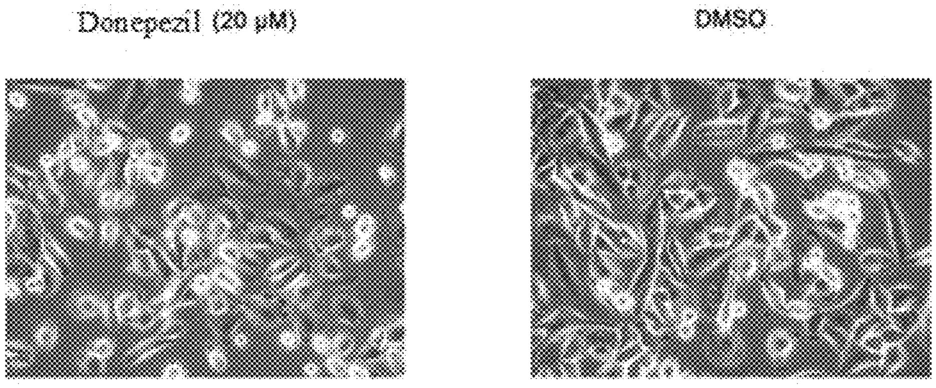
FIG. 4 shows that cholinesterase inhibitors did not induce vacuolation of tumor cells.

2.2 Cholinesterase (AChE) Inhibitors Failed to Induce Vacuolization of Tumor Cells The cholinesterase inhibitor donepezil with a maximum drug concentration of 20 μM failed to induce the vacuolated cell phenotype of the human glioma cell line T98G (FIG. 4).

Figure 5:
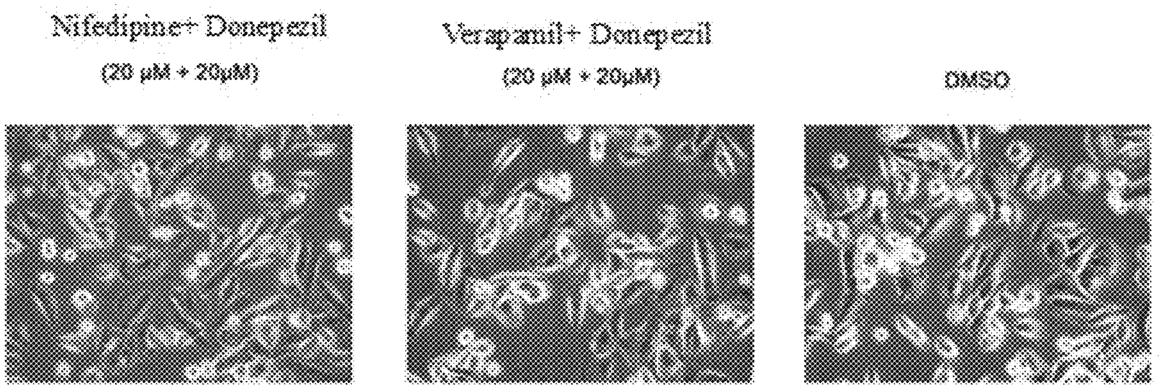
FIG. 5 shows that calcium channel inhibitors combined with cholinesterase inhibitors did not induce vacuolization of tumor cells.

2.3 Calcium Channel Inhibitors in Combination with Cholinesterase Inhibitors Failed to Induce Vacuolization of Tumor Cells The combined use of the calcium channel inhibitor nifedipine or verapamil (20 μM) with the cholinesterase inhibitor donepezil (20 μM) failed to induce the vacuolated cell phenotype in the human glioma cell line T98G (FIG. 5).

Example 4 Study on the Efficacy of S2 on U87MG-Luc Glioblastoma Cell In Situ Transplantation Tumor Model in Nude Mice

1 Materials and Methods

1.1 Experimental Animals

BALB/c nude mice, male, SPF-grade, weighing 20-22 g, were purchased from Shanghai Lingchang Biotechnology Co., Ltd.

1.2 Reagents and Consumables

The information of the main reagents used in this experiment is as follows:

| Name | Cat no./Lot no. | Manufacturer |
|---|---|---|
| D-PBS | H106FA0001 | Sangon Biotech |
| Minimum Essential Medium | 2192505 | gibco |
| MEM NEAA(100×) | 2216384 | gibco |
| Sodium Pyruvate(100 mM) | 2192495 | gibco |
| Fetal Bovine Serum | 2261480CP | gibco |
| 0.05% Trypsin-EDTA | 2192791 | gibco |
| DMSO | 21020207 | TEDIA |
| Double antibodies | 2257223 | gibco |
| 0.9% sodium chloride injection | 1903224C | Anhui Double-Crane Pharmaceutical Co., Ltd. |
| (−)-S2 | D12-20161101-7 | Jiangsu Simovay Pharmaceutical Co., Ltd. |
| Temozolomide (TMZ) | B1828132 | Shanghai Aladdin Biochemical Technology Co., Ltd. |
| Solutol HS-15 (Kolliphor HS-15) | 09362556P0 | Shanghai Chineway Pharmaceutical Excipients Technology Co., Ltd. |
| Ethanol | 20180419 | Sinopharm Chemical Reagent Co., Ltd. |
| Glucose | 20161219 | Sinopharm Chemical Reagent Co., Ltd. |
| Isoflurane | 21101001 | Ruiwode Life Technologies Co., Ltd. |

1.3 Experimental Equipment

The main equipment information in this experiment is as follows:

| Equipment name | Manufacturer | Model | Device number |
|---|---|---|---|
| Analytical Balances | Mettler toledo | XA105 | OW020004 |
| Electronic scale | Changshu G&G Measurement Plant | T1000 type | N/A |
| Small animal live imager | PE | IVIS Lumina XR | N/A |
| Stereotaxic instrument | Stoelting | / | N/A |
| Disposable sterile syringe | Shanghai Misawa Medical Industry Co., Ltd. | 1 mL | N/A |

1.4 Preparation of Drug Solutions

S2

Solvent: 5% ethanol+0.8% Solutol+5% glucose

Preparation method: An appropriate amount of S2 was taken, dissolved with absolute ethanol in proportion under ultrasound, mixed evenly with Solutol HS-15 in proportion under ultrasound (no filamentation phenomenon was observed), slowly added with purified water for dissolution during the ultrasound process, added with glucose in proportion, and dissolved under ultrasound to obtain a solution. The solution was stored at 4° C. in the dark.

1.5 Experimental Methods

1.5.1 Establishment of U87MG-Luc Glioblastoma Cell In Situ Transplantation Tumor Model in Nude Mice Before the transplantation, the U87MG-Luc cells were digested with 0.05%-trypsin-EDTA, resuspended with pre-cooled PBS to $4\times10^7$ cells/mL, and transferred to ice for later use. The nude mice were anesthetized with isoflurane gas, and then fixed on a stereotaxic machine in a prone position. The scalp of the nude mouse was disinfected with iodophor, and incised sagittally with a scalpel. The incision was cleaned with iodophor. The skull was exposed, and drilled with a skull drill extending 1.0 mm in front of the bregma and deviating the right side 2.0 mm. 5 μL of cell suspension ($2\times10^5$ cells) was manually injected with a 10 μL flat-head microsyringe, with inserting the needle to a depth of 3.5 mm, withdrawing the needle 0.5 mm, and injecting for about 10 minutes. After stopping the injection for 5 minutes, the needle was slowly removed, and the incision was sterilized and sutured. Finally 50,000 units of penicillin was injected intramuscularly to prevent infection.

1.5.2 Animal Grouping and Administration

This experiment was divided into 5 groups, namely model group, TMZ group, S2 administration group-LD (0.25 mg/kg), S2 administration group-MD (0.5 mg/kg), S2 administration group-HD (1 mg/kg). The modeled animals were divided into each group in a single-blind manner with equal probability. From the 5th day after the transplantation, the drugs were administered intravenously once a day for 15 days. The model group was given solvent intravenously once a day for 15 days.

1.5.3 In Vivo Imaging of Tumor Cells in the Brain

On days 4, 12, 18, and 25 after the transplantation, 200 μL of 15 mg/mL D-luciferin potassium salt solution, which was filtered and sterilized through a 0.22 μm filter, was injected intraperitoneally. After 10 minutes, IVI chemiluminescence detection (bright field+bioluminescence imaging) was performed using the mouse in vivo imaging system (PE company IVIS Lumina XR). Luorescence intensity was analyzed using Living Image software to obtain fluorescence intensity [p/s], which reflected the size of tumor tissue in the brain of experimental animals.

1.5.4 Animal Survival Period Records

The survival conditions of experimental animals were monitored, and the animals' death dates were recorded timely.

1.6 Data Statistical Analysis

Quantitative data are expressed as mean±standard error. Each pharmacodynamic index was plotted using GraphPad Prism (8.0.1) software, differences between groups were tested by one-way ANOVA or two-way repeat ANOVA, followed by Fisher's LSD test, and survival analysis was performed by Kaplan-Meier. $P<0.05$ was defined as a significant difference.

Figure 6:
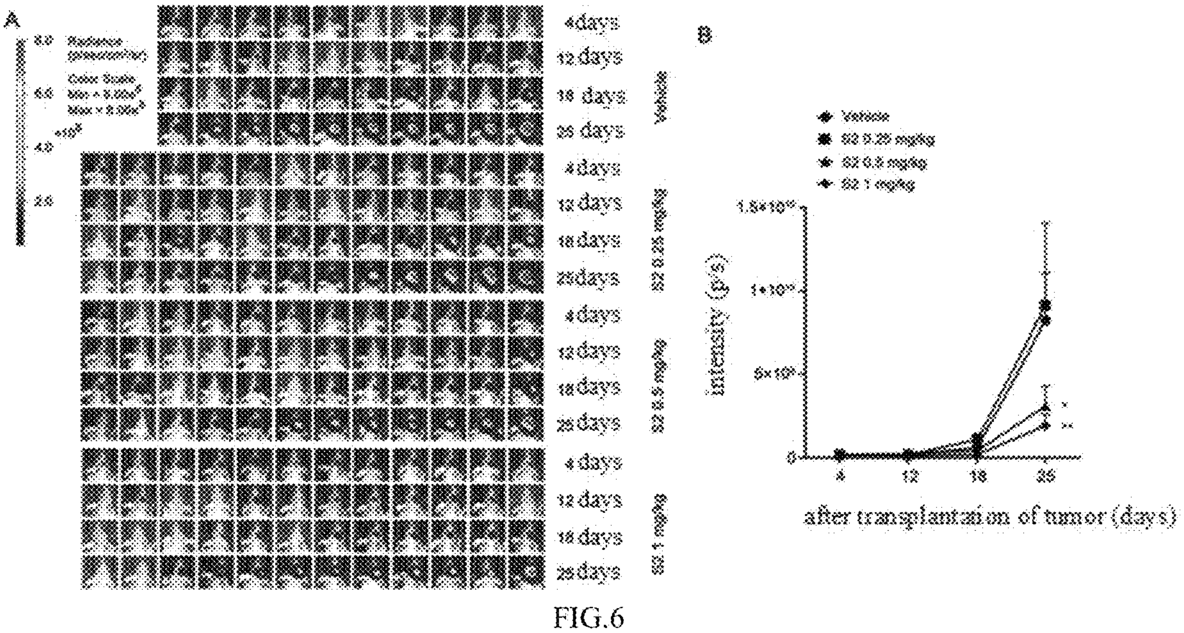
FIG. 6 shows the effect of administration of S2 for 2 weeks on the growth curve of U87MG glioma in the brain of nude mice.
Figure 7:
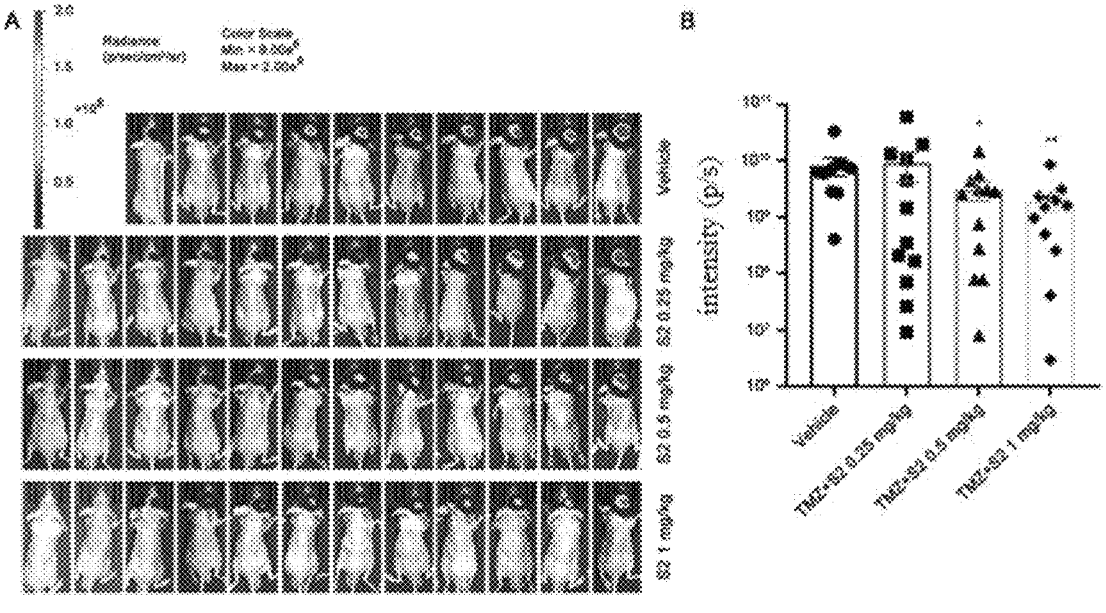
FIG. 7 shows that the administration of S2 for 2 weeks inhibited the growth of U87MG glioma in the brain of nude mice.

2 Experimental Results 2.1 S2 Inhibited the Growth of U87MG Glioma Transplanted In Situ in the Brain of Nude Mice Compared with the vehicle group, both the S2 administration group-MD (0.5 mg/kg, IV) and the S2 administration group-HD (1 mg/kg, IV) could significantly inhibit the growth of U87MG in situ tumors in the brain (FIGS. 6A and B). After two weeks of administration, S2 administration group-MD (0.5 mg/kg, IV) and S2 administration group-HD (1 mg/kg, IV) showed significant inhibitory effect on tumor growth compared with the vehicle group, wherein the S2 administration group-HD (1 mg/kg, IV) had the strongest inhibitory effect on tumor (FIGS. 7A and B).

Figure 8:
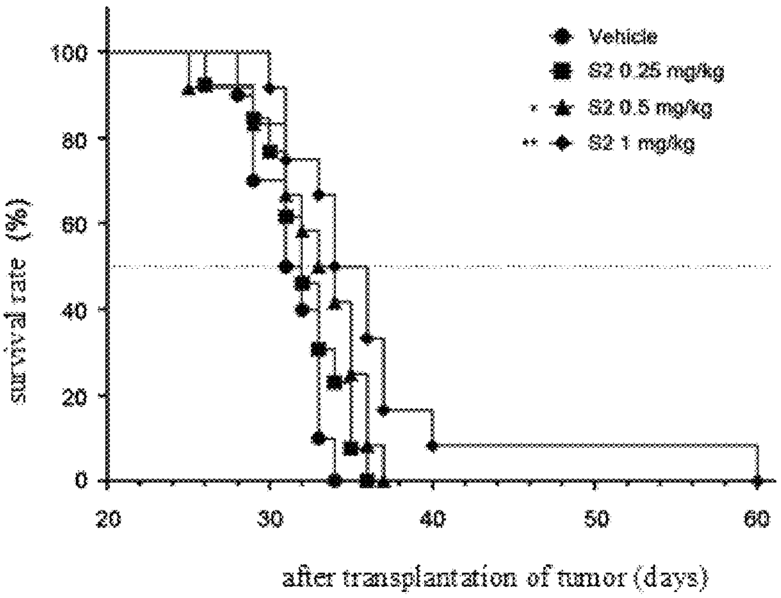
FIG. 8 shows that S2 prolonged the survival period of nude mice with orthotopically transplanted brain glioma.

2.2 S2 Prolonged the Survival Period of Nude Mice with Glioma Transplanted In Situ in the Brain According to the survival curve Log-rank analysis, compared with the vehicle group, S2 administration group-MD (0.5 mg/kg, IV) and S2 administration group-HD (1 mg/kg, IV) significantly increased the survival rate of mice with U87MG brain carcinoma in situ (FIG. 8), prolonged median survival period and overall survival period (Table 4).

TABLE 4

S2 prolonged the survival period of mice with U87MG brain carcinoma in situ

| Survival period | Vehicle | S2 0.25 mg/kg | S2 0.5 mg/kg | S2 1 mg/kg |
|---|---|---|---|---|
| Median survival period (days) | 31.5 | 32.5 | 33.5 | 35 |
| Overall survival period (days) | 31 | 32 | 33 | 36 |

Example 5 Study on the Efficacy of S2 in Combination with Temozolomide (TMZ) on the U87MG-Luc Glioblastoma Cell In Situ Transplantation Tumor Model in Nude Mice 1 Materials and Methods 1.1 Experimental Animals Same as Example 4.

1.2 Reagents and Consumables

Same as Example 4.

1.3 Experimental Equipment

Same as Example 4.

1.4 Preparation of Drug Solutions a) S2

Solvent: 5% ethanol+0.8% Solutol+5% glucose

Preparation method: An appropriate amount of S2 was taken, dissolved with absolute ethanol in proportion under ultrasound, mixed evenly with Solutol HS-15 in proportion under ultrasound (no filamentation phenomenon was observed), slowly added with purified water for dissolution during the ultrasound process, added with glucose in proportion, and dissolved under ultrasound to obtain a solution. The solution was stored at 4° C. in the dark.

b) TMZ

Solvent: 0.9% sodium chloride injection

Preparation method: An appropriate amount of TMZ was weighed, diluted with 0.9% sodium chloride injection in proportion, and shaken until evenly mixed to obtain a solution. The solution was stored at −20° C.

1.5 Experimental Methods 1.5.1 Establishment of U87MG-Luc Glioblastoma Cell In Situ Transplantation Tumor Model in Nude Mice Same as Example 4.

1.5.2 Animal Grouping and Administration

In this experiment, the mice were divided into 4 groups, namely model group, TMZ (3 mg/kg) group, S2+TMZ combined administration group-LD (TMZ 3 mg/kg and S2 0.25 mg/kg), S2+TMZ combined administration group-MD (TMZ 3 mg/kg and S2 0.5 mg/kg) and S2+TMZ combined administration group-HD (TMZ 3 mg/kg and S2 1 mg/kg). The modeled animals were divided into each group in a single-blind manner with equal probability. From the 8th day after the transplantation, TMZ was intraperitoneally administered twice on the 8th and 15th days; S2 was intravenously administered once a day for 15 days.

1.5.3 In Vivo Imaging of Tumor Cells in the Brain

On days 7, 14, and 21 after the transplantation, 200 μL of 15 mg/mL D-luciferin potassium salt solution, which was filtered and sterilized through a 0.22 μm filter, was injected intraperitoneally. After 10 minutes, IVI chemiluminescence detection (bright field+bioluminescence imaging) was performed using the mouse in vivo imaging system (PE company IVIS Lumina XR). Luorescence intensity was analyzed using Living Image software to obtain fluorescence intensity [p/s], which reflected the size of tumor tissue in the brain of experimental animals.

1.5.4 Animal Survival Records

The survival conditions of experimental animals were monitored, and the animals' death dates were recorded timely.

1.6 Data Statistical Analysis

Quantitative data are expressed as mean±standard error. Each pharmacodynamic index was plotted using GraphPad Prism (8.0.1) software, differences between groups were tested by one-way ANOVA or two-way repeat ANOVA, followed by Fisher's LSD test, and survival analysis was performed by Kaplan-Meier. $P<0.05$ was defined as a significant difference.

Figure 9:
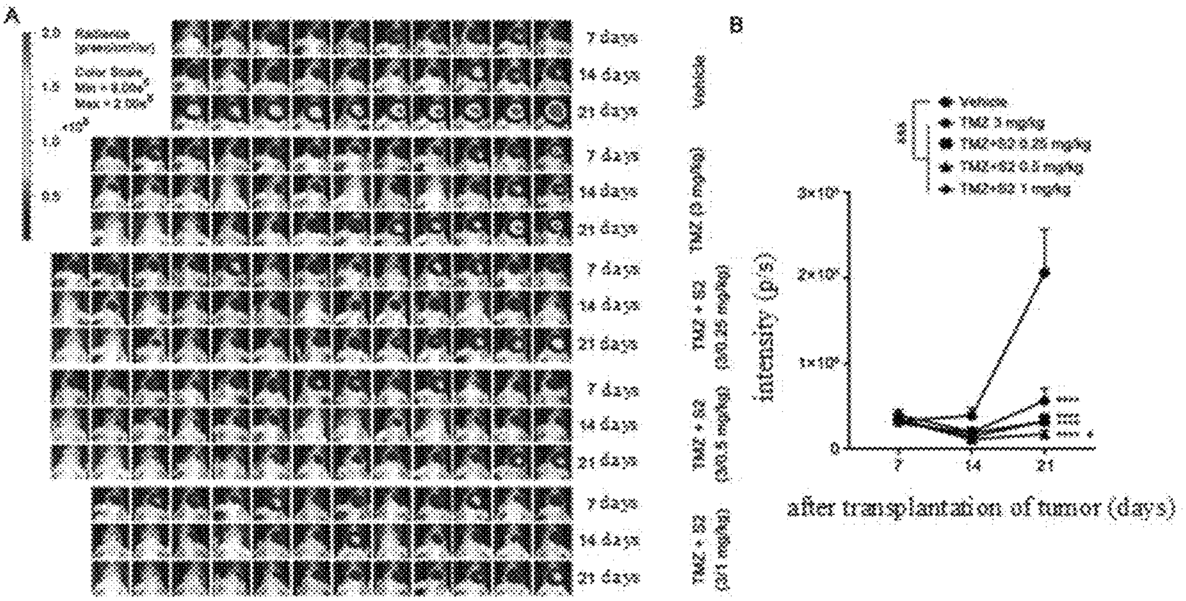
FIG. 9 shows the effect of S2+TMZ combined treatment for 2 weeks on the growth curve of U87MG glioma in the brain of nude mice.
Figure 10:
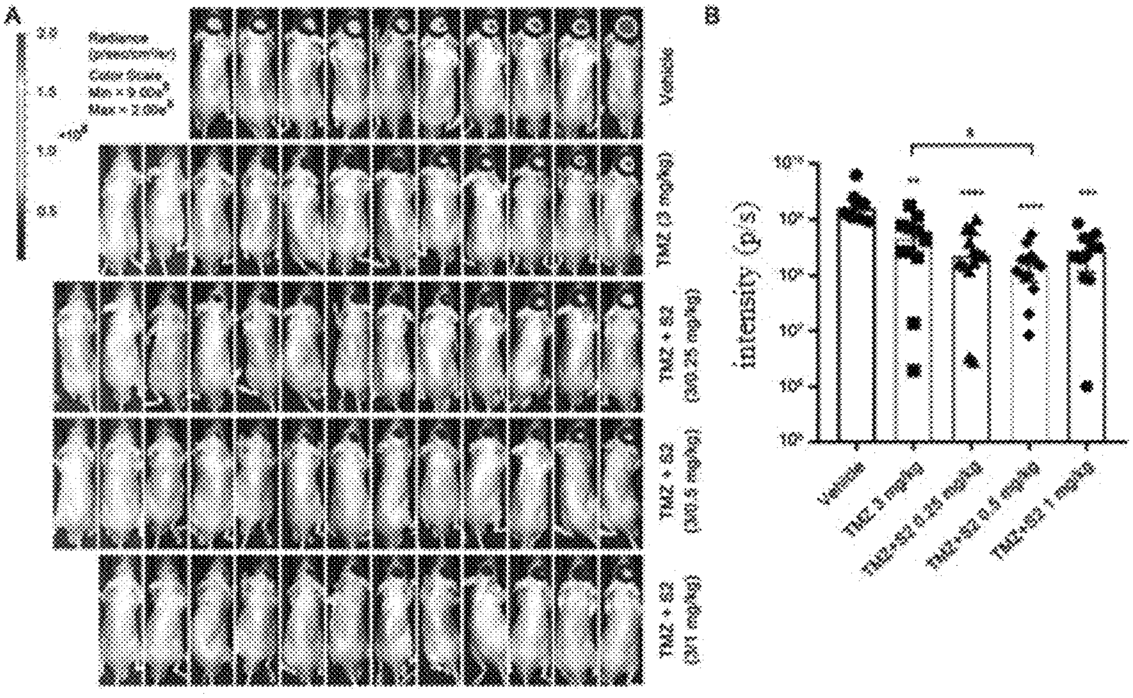
FIG. 10 shows the effect of S2+TMZ combined treatment for 2 weeks on the growth of intracerebral glioma.

2 Experimental Results 2.1 Effect of S2+TMZ Combination on the Growth of U87MG Glioma in the Brain of Nude Mice Compared with the vehicle group, TMZ (3 mg/kg, IP) administration alone and TMZ+S2 (0.25, 0.5, and 1 mg/kg IV) combined administration could both significantly inhibit the growth of U87MG in situ tumor in the brain (FIGS. 9A and B). After 2 weeks of administration (day 21), compared with TMZ, the S2+TMZ combined administration group showed stronger inhibitory effect on tumor growth, and the tumor inhibitory effect of the S2 (0.5 mg/kg)+TMZ combined administration group was significantly better than that of the TMZ group (FIGS. 10A and B).

Figure 11:
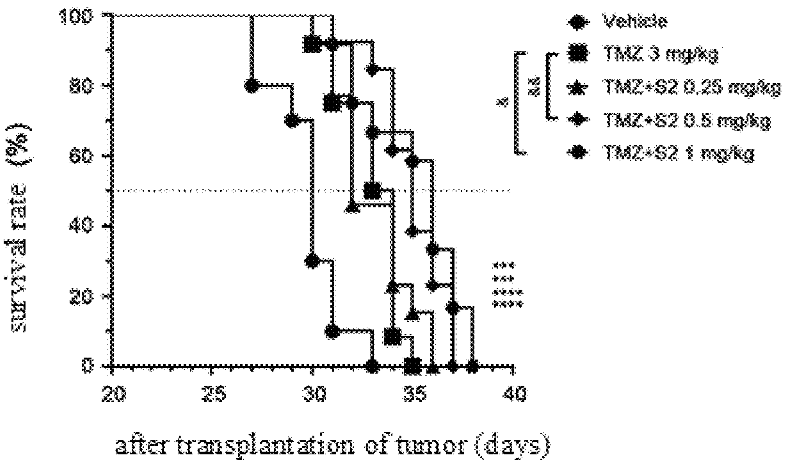
FIG. 11 shows that the S2+TMZ combined treatment prolonged the survival period of mice with U87MG brain carcinoma in situ.

2.2 Effect of S2+TMZ Combination on Survival of Nude Mice with In Situ Glioma in Brain According to the survival curve Log-rank analysis, compared with the vehicle group, there was a significant difference in the survival period of mice between the TMZ (3 mg/kg, IP) alone group and TMZ+S2 (0.25, 0.5 and 1 mg/kg IV) combined administration group. Compared with TMZ administration alone, the combination of S2 (0.5 mg/kg)+ TMZ and S2 (1 mg/kg)+TMZ significantly increased the survival rate of mice with U87MG brain carcinoma in situ (FIG. 11) and prolonged the median survival period and overall survival period (Table 5).

TABLE 5

The combined use of S2 + TMZ prolonged the survival period of mice with U87MG brain carcinoma in situ.

| Survival period | Vehicle | TMZ 3 mg/kg | TMZ + S2 0.25 mg/kg | TMZ + S2 0.5 mg/kg | TMZ + S2 1 mg/kg |
|---|---|---|---|---|---|
| Median survival period (days) | 30 | 33.5 | 32 | 35 | 36 |
| Overall survival period (days) | 33 | 35 | 36 | 37 | 38 |

Example 6 In Vivo Pharmacodynamic Study of S2 on Human Brain Glioma T98G in NOD SCID Mouse Subcutaneous Model 1 Methods and Materials 1.1 Experimental Animals NOD SCID, female, 6-8-week old, weighing 18-21 g, were purchased from Beijing VitalRiver Experimental Animal Technology Co., Ltd.

1.2 Tested Drugs

Temozolomide (TMZ), Shanghai Aladdin Biochemical Technology Co., Ltd., batch number: B1828132.

S2, Jiangsu Simovay Pharmaceutical Co., Ltd., batch number: D12-20161101-7.

1.3 Preparation of Drug Solutions

Preparation method of TMZ (1.5 mg/mL): 18 mg of Temozolomide was weighed and dissolved in 12 mL of 1% HPMC.

The preparation method of S2 administration solution was the same as that in Example 4.

1.4 Experimental Methods 1.4.1 Establishment of T98G Glioblastoma Cells Subcutaneous Transplantation Tumor Model in Nude Mice Human brain glioma T98G cells were cultured in vitro. The cells were cultured in EMEM medium added with 10% fetal calf serum, 100 U/mL penicillin and 100 g/mL streptomycin, in a 37° C. 5% $CO_2$ incubator. After the number of cells reached the required number, the cells were collected. 0.2 mL ($10\times10^6$) of T98G tumor cells (PBS:Matrigel=1:1) were subcutaneously inoculated into the right back of each mouse. The mice were grouped and administered when the average tumor volume reached approximately 147 $mm^3$.

1.4.2 Animal Grouping and Administration

The first set of experiments was divided into two groups, namely: vehicle group and TMZ group (15 mg/kg, PO); the modeled animals were randomly divided into each group in a single-blind manner, with 10 animals in each group.

The second set of experiments was divided into two groups, namely: vehicle group and S2 group (3 mg/kg, IV); the modeled animals were randomly divided into each group in a single-blind manner, with 9 animals in each group.

1.4.3 Measurement of Tumor Size

Tumor diameters were measured with vernier calipers twice a week, and tumors were weighed and photographed after the experiment.

1.5 Data Statistics The tumor volume was calculated as follows: $V=0.5a\times b^2$, where a and b represent the long and short diameters of the tumor respectively.

The tumor inhibitory effect was evaluated by TGI (%) or relative tumor proliferation rate T/C (%).

The tumor inhibitory effect was calculated as TGI (%): TGI %=[1-(average tumor volume at the end of administration in a certain treatment group−average tumor volume at the beginning of administration in the treatment group)/(average tumor volume at the end of administration in the vehicle control group−average tumor volume in the vehicle control group at the beginning of treatment)]×100.

Relative tumor proliferation rate T/C (%): T/C %=TRTV/CRTV×100 (TRTV:RTV of treatment group; CRTV:RTV of negative control group). The relative tumor volume (RTV) was calculated based on the results of tumor measurement according to the calculation formula of $RTV=V_t/V_0$, where $V_0$ is the average tumor volume measured at the time of grouping and administration (i.e. $d_0$), and $V_t$ is the average tumor volume of the measurement at a certain time, $T_{RTV}$ and $C_{RTV}$ are taken on the same day.

Statistical analysis was based on the mean and standard error (SEM) of tumor volumes in each group at the end of the experiment. Comparisons between two groups were analyzed using T-test. All data analysis was performed with GraphPad Prism (8.0.1), and P<0.05 was considered to be a significant difference.

2 Experimental Results

Figure 12:
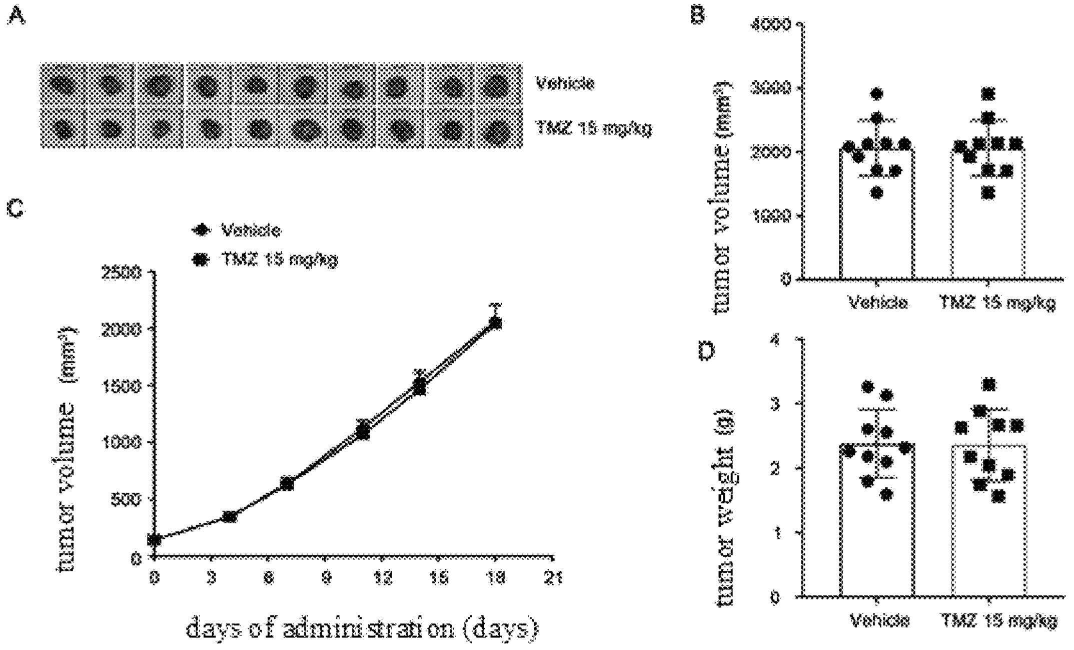
FIG. 12 shows that TMZ could not inhibit the growth of T98 glioma and could not reduce the volume and weight of solid tumors.

2.1 Effect of TMZ on T98 Tumor Growth and Tumor Weight at Experimental Endpoint Compared with the vehicle group, the TMZ 15 mg/kg group had no inhibitory effect on tumor volume growth (FIGS. 12A-C). Tumors were collected and weighed at the end of the experiment. There was no significant difference in tumor weight between the TMZ 15 mg/kg group and the control group (FIG. 12D), which was consistent with the above tumor volume inhibition.

Figure 13:
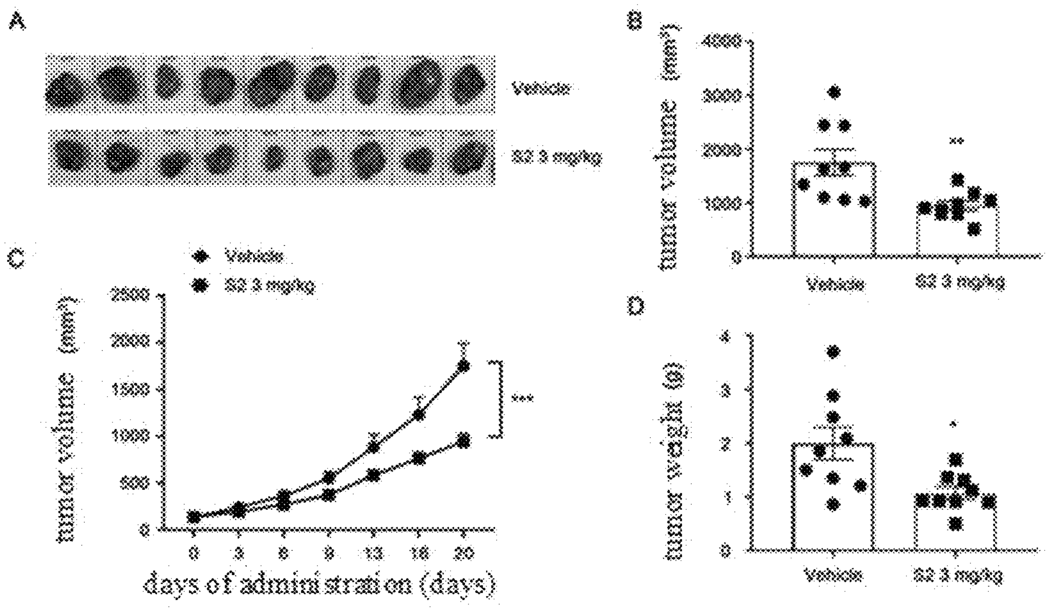
FIG. 13 shows that S2 inhibited the growth of T98 glioma and reduced the volume and weight of solid tumors.

2.2 Effect of S2 on T98 Tumor Growth and Tumor Weight at Experimental Endpoint Compared with the vehicle group, the S2 3 mg/kg group significantly inhibited tumor volume growth (FIGS. 13A-C). Tumors were collected and weighed at the end of the experiment. The tumor weight in the S2 3 mg/kg group was significantly lower than that in the control group (FIG. 13D), which is consistent with the above-mentioned tumor volume inhibition.

The invention claimed is:

1. A method of treating a tumor, comprising administering a 1,4-dihydro-naphthyridine derivative represented by Formula I or a pharmaceutically acceptable salt thereof to a subject in need thereof, Formula I

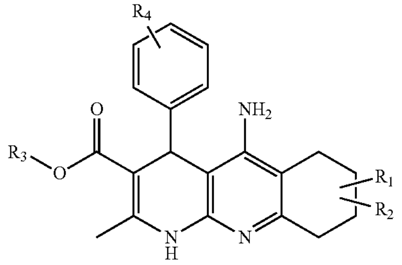

wherein, $R_1$ or $R_2$ is hydrogen, halogen or $C_1$-$C_6$ alkyl;

$R_3$ is selected from $C_1$-$C_6$ alkyl, wherein any-$CH_2$-in the alkyl may be replaced by one or more —O—;

$R_4$ is hydrogen or halogen.

2. A method of treating a tumor, comprising administering a 1,4-dihydro-naphthyridine derivative or a pharmaceutically acceptable salt thereof in to a subject in need thereof, wherein the compound is selected from the group consisting of:

S1

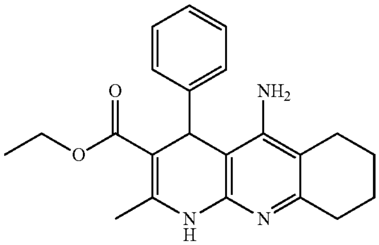

Compound 1 represented by S1;

S2

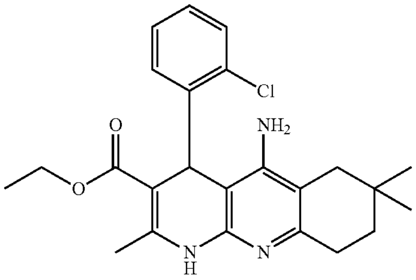

Compound 2 represented by S2;

S3

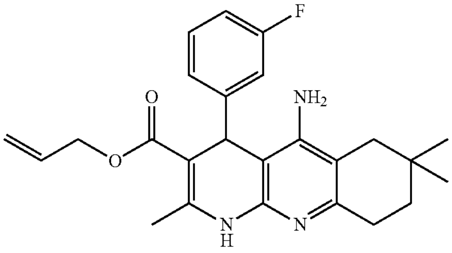

Compound 3 represented by S3;

S4

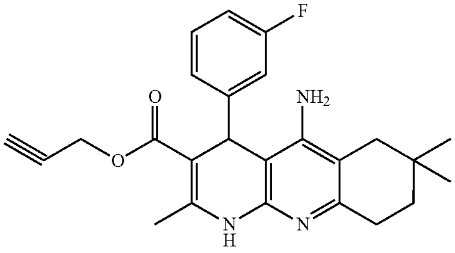

Compound 4 represented by S4;

S5

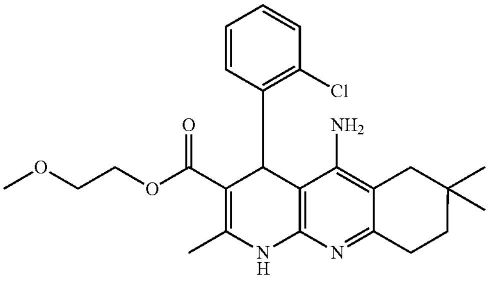

Compound 5 represented by S5; and

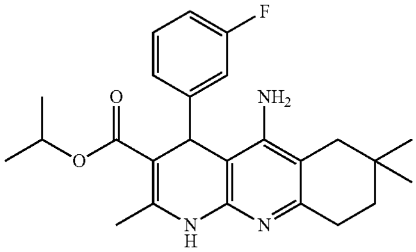

S6

Compound 6 represented by S6.

3. The method according to claim 2, wherein the 1,4-dihydro-naphthyridine derivative is used for treating a solid tumor.

4. The method according to claim 2, wherein the 1,4-dihydro-naphthyridine derivative is used for treating a nervous system tumor.

5. The method according to claim 2, wherein the 1,4-dihydro-naphthyridine derivative is used for treating a brain tumor.

6. The method according to claim 2, wherein the 1,4-dihydro-naphthyridine derivative is used for treating a glioma.

7. The method according to claim 2, wherein the 1,4-dihydro-naphthyridine derivative is used for treating a glioblastoma.

8. The method according to claim 2, wherein the 1,4-dihydro-naphthyridine derivative is used for treating liver cancer, colon cancer and gastric cancer.

9. The method according to claim 2, wherein the 1,4-dihydro-naphthyridine derivative is used in combination with temozolomide for treating a glioma.

10. The method according to claim 2, wherein the 1,4-dihydro-naphthyridine derivative is used in combination with radiotherapy for treating a glioma.

* * * * *